United States Patent [19]

Erickson et al.

[11] Patent Number: 5,351,389
[45] Date of Patent: Oct. 4, 1994

[54] METHOD FOR FABRICATING A CONTOURED TRIANGULAR TRANSDUCER SYSTEM

[75] Inventors: John H. Erickson, Plano; John C. Tepper, Carrollton, both of Tex.

[73] Assignee: AMEI Technologies Inc., Wilmington, Del.

[21] Appl. No.: 973,681

[22] Filed: Nov. 9, 1992

Related U.S. Application Data

[62] Division of Ser. No. 638,219, Jan. 7, 1991, Pat. No. 5,195,941.

[51] Int. Cl.$^5$ .......................... H01F 7/06; A61N 2/00
[52] U.S. Cl. .............................. 29/605; 600/9
[58] Field of Search ..................... 600/9–15; 29/592.1, 602.1, 606, 623.4, 623.5, 605

[56] References Cited

U.S. PATENT DOCUMENTS

| | | | |
|---|---|---|---|
| 4,501,265 | 2/1985 | Pescatore | 128/15 |
| 4,616,629 | 5/1985 | Moore | 128/15 |
| 4,654,574 | 3/1987 | Thaler | 320/14 |
| 4,818,697 | 4/1989 | Liboff et al. | . |
| 4,819,322 | 4/1989 | Higuchi et al. | 29/606 |
| 4,932,951 | 6/1990 | Liboff et al. | . |
| 4,998,339 | 3/1991 | Wiesner | 29/602.1 |
| 5,045,050 | 9/1991 | Liboff et al. | . |
| 5,059,298 | 10/1991 | Liboff | . |
| 5,067,940 | 11/1991 | Liboff et al. | . |
| 5,084,958 | 2/1992 | Yerman et al. | 29/602.1 |
| 5,087,336 | 2/1992 | Liboff et al. | . |
| 5,106,361 | 4/1992 | Liboff et al. | . |
| 5,123,898 | 6/1992 | Liboff et al. | . |
| 5,139,474 | 8/1992 | Lamond et al. | . |
| 5,142,767 | 9/1992 | Adams et al. | 29/602.1 |
| 5,143,588 | 9/1992 | Liboff et al. | . |
| 5,160,591 | 11/1992 | Liboff et al. | . |
| 5,170,544 | 12/1992 | Pichl | 29/602.1 |
| 5,183,456 | 2/1993 | Liboff et al. | . |

FOREIGN PATENT DOCUMENTS 11986   1/1991   France ........................... 600/13

Primary Examiner—Lee S. Cohen
Assistant Examiner—J. P. Lacyk
Attorney, Agent, or Firm—Baker & Botts

[57] ABSTRACT

Fabricating a transducer system (FIGS. 1a–1b) for providing electromagnetic therapeutic stimulation to a target area of a patient's body includes forming a primary winding (71) having a selected number of turns. The primary winding (71) and any other windings (72, 73) are bonded together to form a winding bundle (32). The winding bundle (32) is encapsulated in a malleable shell (34) that is substantially triangular in shape. Control electronics (16, 40, 94) are coupled to the shell-encapsulated winding bundle (30, 70, 90) for selectively generating electromagnetic fields, and thus implementing a prescribed electromagnetic therapy.

16 Claims, 2 Drawing Sheets

METHOD FOR FABRICATING A CONTOURED TRIANGULAR TRANSDUCER SYSTEM

RELATED APPLICATION

This application is a divisional of application Ser. No. 07/638,219 (Attorney's Docket 90928-9991), filed Jan. 7, 1991 and entitled Contoured Triangular Transducer System for PEMF Therapy, now U.S. Pat. No. 5,195,941, issued Mar. 23, 1993.

This application is related to a co-pending U.S. patent application, Ser. No. 07/586,505 (Attorney's Docket 90928-0090), entitled Double-Transducer System for PEMF Therapy, which was filed on Sep. 21, 1990, now U.S. Pat. No. 5,181,902, and is assigned to the assignee of this application.

TECHNICAL FIELD OF THE INVENTION

The invention relates generally to pulsed electromagnetic field (PEMF) therapy, and more particularly relates to a PEMF system that uses an anatomically contoured triangular transducer to provide PEMF therapeutic stimulation to a target area of the skeletal system (such as the neck and upper spine), and a method of fabricating the system.

BACKGROUND OF THE INVENTION

Pulsed electromagnetic fields (PEMF) are low-energy, time-varying magnetic fields that are used to treat therapeutically resistant problems of the musculoskeletal system. Those problems include spinal fusion, ununited fractures, failed arthrodeses, osteonecrosis, and chronic refractory tendonitis, decubitus ulcers and ligament, tendon injuries, osteoporosis, and Charcot foot.

The specific problem to which the invention is directed is an improved PEMF spinal stimulation system for providing PEMF therapeutic stimulation to the cervical (neck) area of the spinal column undergoing fusion or other repair (such as treatment to salvage a failed fusion).

For cervical PEMF therapy, an electromagnetic transducer coil is placed in back of the patient's neck such that pulsing the transducer produces an applied or driving field that penetrates to the cervical spine. The conventional approach has been to attach to a cervical collar an oval shaped transducer coil for positioning on the back of the neck. This approach is disadvantageous in that the electromagnetic field is significantly nonuniform, and that the transducer coil does not cover (and therefore the electric field does not penetrate) below the vertebrae at the bottom of the neck.

Accordingly, a need exists for an improved PEMF system that provides a more uniform field to the target area, such as the cervical spine.

SUMMARY OF THE INVENTION

The present invention is a PEMF contoured triangular transducer system that takes advantage of flux-aiding to achieve improved field uniformity. In an exemplary embodiment, the semi-rigid transducer is anatomically contoured for positioning around the back of the neck.

In one aspect of the invention, the PEMF contoured triangular transducer system includes a transducer including at least a primary winding with a selected number of turns encased in a shell that is at least semi-rigid. The transducer, which when flat is substantially triangular in shape, is anatomically contoured for positioning over the target area for PEMF therapy, with at least one side of the transducer being curved such that first and second angles are located substantially on either side of the target area. Activation electronics are coupled to the primary winding of both transducers for selectively generating electromagnetic fields to implement a prescribed PEMF therapy program (such as for post-fusion repair).

In more specific aspects of the invention, the PEMF contoured triangular transducer system is used in an exemplary embodiment to provide PEMF therapy for the cervical spine. The transducer is anatomically contoured by curving a side of the transducer in conformance with the back of the neck, such that the first and second angles are positioned on substantially opposite sides of the neck, with the third angle being located in the middle of the back just below the neck.

The contoured triangular transducer includes both primary and secondary windings, and a sense winding, and the drive electronics includes an energy recovery circuit. The secondary windings and the energy recovery circuit are active during a de-energization cycle to recover energy (conserving battery power)—the secondary winding is also used to tailor the parameters of the electromagnetic field.

The primary, secondary and sense windings are flat wound, permitting the shell to be formed with a substantially flat cross sectional profile. The shell is a semi-rigid shell made of formable polyurethane elastomer, flexible enough to permit a patient to alter the anatomical contoured of the transducer for maximum comfort.

Activation circuitry includes separate control and drive electronics—the control electronics are located in a separate control electronics module, while the drive electronics are encapsulated into the transducer shell. The control electronics includes a PEMF processor that executes a PEMF program for controlling the activation of the electromagnetic fields (field strength and duty cycle). In addition to implementing the PEMF therapy program, the PEMF processor collects appropriate data in memory to enable the attending health care professional to monitor the course of the therapy.

The exemplary contoured cervical transducer is fabricated as follows. Primary, secondary and sense windings of adhesive coated magnet wire are wound around a flat mandrel with an appropriate triangular shape for the contoured triangular transducer. The windings are bonded by heat curing the adhesive to obtain a flat-wound flexible winding bundle. The winding bundle, along with a drive electronics board, are placed in a mold, and encapsulated in a semi-rigid shell. A bending fixture is used to configure the transducer with the selected anatomical contour.

In another exemplary embodiment, the contoured triangular transducer is anatomically contoured for positioning over a shoulder. As with the exemplary cervical embodiment, the transducer is contoured such that first and second angles wrap around the shoulder for positioning in the front and back of the shoulder.

The technical advantages of the invention include the following. The PEMF contoured triangular transducer system includes a transducer that is anatomically contoured around a target area for PEMF therapy, providing magnetic flux-aiding to optimize the electromagnetic field available for stimulating the target area, and to reduce system power consumption. The semi-rigid transducer is configured with an anatomical contour, and can be configured with a substantially flat cross sectional profile that provides a broad contact area. In particular, for the cervical spine application, the triangular transducer extends down the spinal column, between the shoulder blades, providing coverage for the vertebrae at the bottom of the neck and the top of the back. The transducer is formable with a selected degree of rigidity, and is conformable without any special conforming assembly or process (such as heat), thereby enabling the patient or health care provider to customize or alter the anatomical contour. Programmable control electronics implement a PEMF program that appropriately controls electromagnetic field activation according to a predetermined PEMF therapeutic regimen, and that stores appropriate data for monitoring the progress of the PEMF therapy.

BRIEF DESCRIPTION OF THE DRAWINGS

For a more complete understanding of the invention, and for further features and advantages, reference is now made to the following Detailed Description of an exemplary embodiment of the invention, taken in conjunction with the accompanying Drawings, in which.

DETAILED DESCRIPTION OF THE INVENTION

The Detailed Description of a exemplary embodiments of the PEMF contoured triangular transducer system is organized as follows:
1. Cervical Transducer System
2. Transducer Fabrication
3. Control and Drive Electronics
4. Shoulder Embodiment
5. Conclusion The exemplary embodiments of the PEMF contoured triangular transducer system are configured to provide PEMF therapy for the cervical spine or neck, and the shoulder, such as for fusion repair.

1. Cervical Transducer System

Figure 1A:
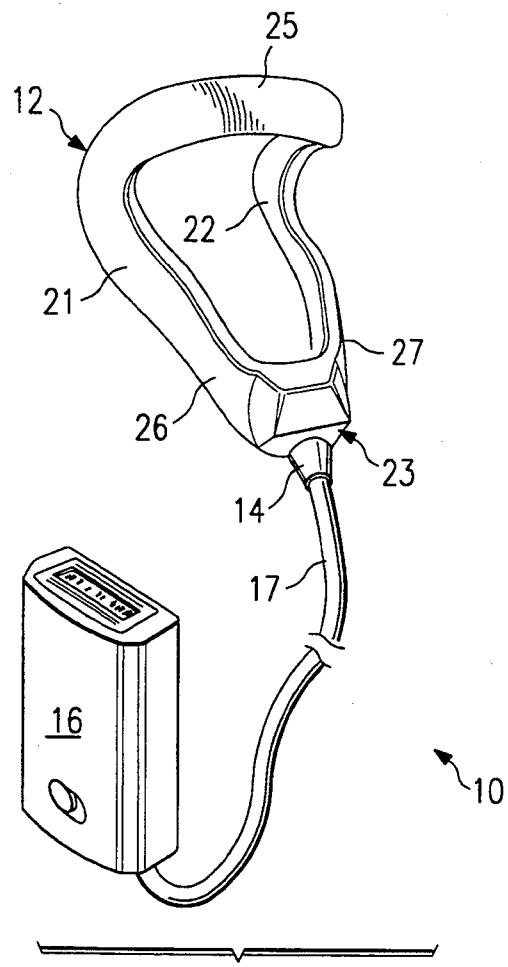
FIGS. 1a-1b illustrate an exemplary PEMF contoured triangular transducer system according to the exemplary embodiment of the invention.
Figure 1B:
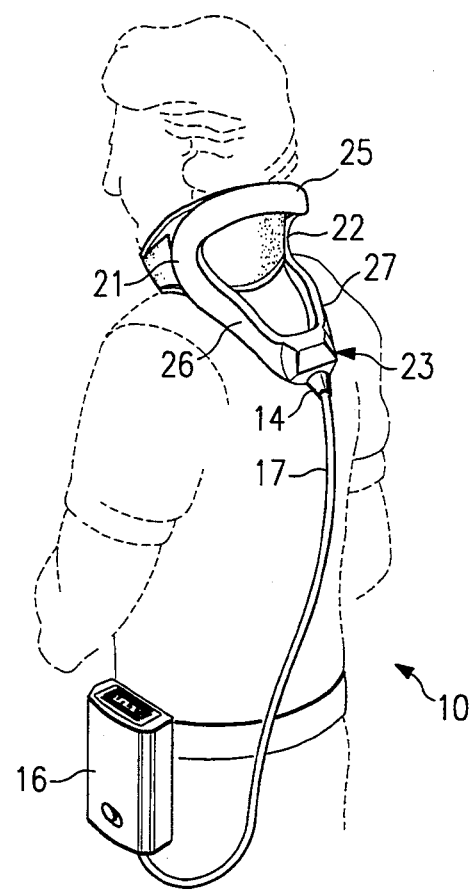

FIGS. 1a-1b illustrate an exemplary PEMF contoured triangular transducer system 10 for cervical PEMF therapy. The system comprises three principal components: (a) a contoured triangular transducer 12; (b) encapsulated drive electronics 14 integral with the contoured triangular transducer; and (c) a control electronics module 16 coupled to the drive electronics by a cable 17.

The contoured triangular transducer is configured so that, when flat, it is substantially triangular in shape, such that it defines two neck angles 21 and 22 and a back angle 23, connected by three sides 25, 26, and 27.

The transducer 12 has an anatomical contour that, as shown particularly in FIG. 1b, is configured for positioning on the back of the patient's neck. That is, side 25 is curved to fit around the back of the neck so that the neck angles 21 and 22 are positioned on opposite sides of the neck, while the sides 26 and 27 are slightly curved to extend over the back of the shoulders so that the back angle 23 is positioned in the middle of the back between the shoulder blades. Thus, the triangular contour permits the transducer to cover the vertebrae of the neck and the portion of the spine between the shoulder blades.

The exemplary contoured triangular transducer has a substantially flat cross sectional profile (see FIG. 2), which is a result of its flat-wound construction. The contoured triangular transducer is semi-rigid to maintain the selected contour and profile, although the transducer is bendable by the patient or health care professional to customize or alter the anatomical contour. As described in Section 2, the transducer includes flat-wound primary, secondary and sense windings encapsulated in a shell of a plasticized elastomer material (such as polyurethane) with a selected degree of rigidity.

The transducer includes both primary and secondary windings, with the secondary windings being used to provide energy recovery, and as a collateral function, to assist in tailoring the electromagnetic field output from the transducers. Alternatively, the advantages of the PEMF contoured triangular transducer system of the invention for implementing a PEMF therapy could be obtained using only a primary winding (i.e., with no energy recovery windings, but preferably with an alternative efficient programmed energy format).

Drive electronics 14 is encapsulated into the shell of the contoured triangular transducer in the area of the back angle 23. A small circuit board carrying the drive electronics is coupled both to the primary, secondary and sense windings of the contoured triangular transducer, and through the cable 17 to the control electronics module 16.

The control electronics module 16 is carried by the patient by a shoulder strap (not shown), or alternatively by a belt. It includes a PEMF processor for providing pulsing current to the front and back transducers at predetermined intervals, thereby activating the electromagnetic field according to a prescribed preprogrammed PEMF regimen.

To implement a PEMF therapy program, a health care professional determines a PEMF therapy that includes a regimen of PEMF stimulation of the neck. The prescribed PEMF therapy regimen is translated into a PEMF program, which is programmed into a PEMF memory in the control electronics, either during manufacture or subsequently.

For patient use, the contoured triangular transducer is placed into a velfoam pouch or other soft covering (not shown), and then attached to a soft cervical collar (not shown) preferably using velcro fasteners. As stated above, the semi-rigid transducer shell is sufficiently flexible to permit the patient or a health care professional to adjust the anatomical contour. This arrangement relies on the soft cervical collar for support, with the PEMF transducer being contoured around the collar.

To commence a PEMF therapy session, the patient puts on the cervical collar with the contoured triangular transducer attached. Once the PEMF system is in place, the patient starts the PEMF program by turning on the control electronics module.

In accordance with the stored PEMF therapy program, the PEMF processor correspondingly controls the activation current supplied to the transducers, thereby controlling the electromagnetic fields in terms of energization time, de-energization time, and duty cycle (repetition rate). In addition to controlling the PEMF therapy, the PEMF processor maintains treatment data that is available on request to the patient (through a small display), and to a health care professional (via an I/O port) for monitoring and analysis.

2. Transducer Fabrication

For an exemplary embodiment, the contoured triangular transducer is fabricated in a flat wound configuration as follows.

Figure 2:
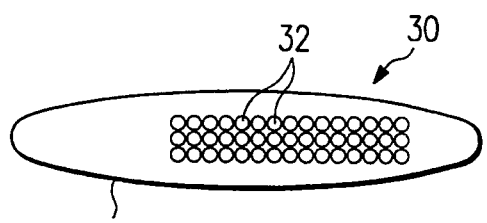
FIG. 2 is a cross sectional view of the transducer showing the flat-wound bundle of windings, and the encapsulating shell.

FIG. 2 is a cross sectional view of a transducer that includes primary, secondary and sense windings 32 encapsulated in a semi-rigid shell 34. The primary, secondary and sense windings are not shown differentiated in the FIGURE, nor is the total number of windings shown meant to be accurate—the FIGURE is illustrative only.

For the exemplary embodiment, a transducer includes two parallel primary windings of about 7 turns each, a secondary winding of about 35 turns, and a sense winding of at least 1 turn. For the primary and secondary windings, 18 gauge wire can be used, while 22 gauge wire can be used for the sense winding. The approximate dimensions of the winding bundle are 0.75 by 0.12 inches, while the approximate dimensions of the shell are 1.50 by 0.31 inches.

The winding material is a commercially available magnet wire that includes an overcoat of an adhesive, such as polyurethane adhesive coated wire. The shell is a polyurethane-type elastomer material, also available commercially. Other shell materials can be used to provide different degrees of transducer-shell rigidity, thereby providing different bracing rigidity characteristics.

The adhesive-coated primary, secondary and sense windings are wound simultaneously in a winding machine around a flat mandrel of the appropriate triangular shape for the transducer. The windings are maintained in the flat-wound position shown in the FIGURE by parallel sideplates. Once wound, the start and finish wire ends for each winding are cut to provide leads for coupling to the drive electronics, and the winding assembly—winding bundle, mandrel and sideplates—is removed from the winding machine.

The winding assembly is then placed in an oven for heat curing at the appropriate curing temperature. Heat curing activates the adhesive coating, and the windings are bonded together to form the winding bundle 32. The winding assembly is removed from the oven and, after cooling, a sideplate is removed, allowing the bonded winding bundle to be removed. The winding bundle is now in a flexible, bonded unit.

Next, the circuit board (not shown) with the drive electronics is positioned in the area of one angle, and secured in place such as by adhesive tape. The winding leads of the transducer and the wires of a cable are attached to the drive electronics board, such as by soldering.

The winding bundle 32 is placed in a substantially flat mold of the appropriate shape, with the cable extending through a strain relief exit in the mold. The polyurethane type elastomer material is then introduced into the mold, encapsulating the transducer winding bundle and the drive electronics board, and forming the semi-rigid shell 34.

For the exemplary embodiment, a two component polyurethane elastomer is used: an isocyanate and a polyol. In a vacuum, the two components are mixed, and then poured into the mold, covering the winding bundle. These steps are performed in a vacuum to eliminate entrapped air which can cause voids that reduce structural integrity and are cosmetically undesirable. The mold is placed in an oven for heat curing the polyurethane type elastomer material to form the encapsulating shell 34.

After cooling, the potted transducer shell, with the attached cable, is removed from the mold. The transducer is cleaned of mold release, and any flash is trimmed off.

Finally, the transducer is placed in a bending fixture, and bent into the desired anatomical contour. The completed semi-rigid transducer is now ready to be inserted into a velfoam pouch and attached to a cervical collar, with the cable being coupled to the control electronics module.

3. Control and Drive Electronics

Figure 3:
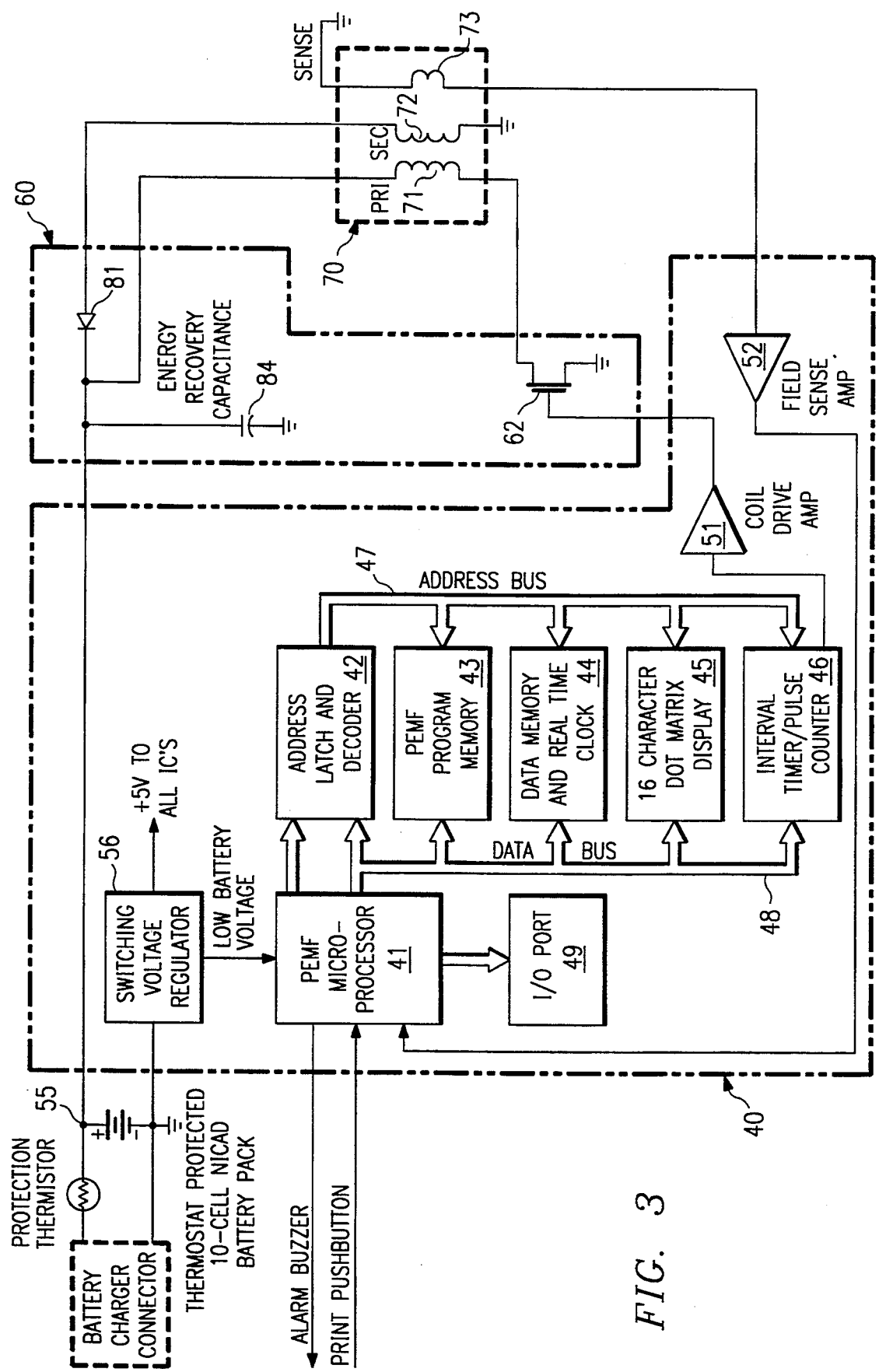
FIG. 3 is a schematic block diagram of the control electronics and the drive electronics.

FIG. 3 is a schematic block diagram of the control and drive electronics, which are physically located respectively in the control electronics module (16 in FIG. 1a) and encapsulated within the shell of the contoured triangular transducer (at 23 in FIG. 1a).

Control electronics 40 includes a PEMF processor 41, with associated IC (integrated circuit) components: an address latch and decoder circuit 42, a PEMF program memory 43, a data memory and real time clock circuit 44, a 4-character, 7-segment display module 45 and an interval timer/pulse counter 46. The PEMF processor is coupled to these components by an address bus 47 and a data bus 48.

A PEMF program can be loaded into an EPROM or other memory and installed as PEMF program memory 43; alternatively, the PEMF program can be read into the PEMF program memory via an I/O port 49. Data collected during execution of the programmable PEMF program parameters—such as start time, stop time, duration, and daily average—is stored in the data memory 44, and can be read out to a printer (or over a communications link) via the I/O port 49.

The PEMF processor 41 and the interval timer/pulse counter 46 control a transducer drive amplifier 51. The coil drive amplifier controls the energation and de-energation of the triangular transducer. A field sense amplifier 52 is used to sense the resulting electromagnetic fields and provide an appropriate signal to the PEMF processor.

The PEMF processor 41 receives power from a Dower source, such as a NICAD battery pack 55, through a switching voltage regulator 56 (which also provides +5 volts power to the other IC components).

PEMF processor 41, and the supporting IC CMOS logic chips and display module, function conventionally and are commercially available. For the exemplary embodiment, PEMF processor 41 is an RCA 1806 processor. The address latch and decoder IC 42 is a type 1873. The PEMF program memory is a 2816 2 Kbyte EEPROM that is loaded with a PEMF program during manufacture. The data memory and real time clock IC 44 is a Mostek MK48T02, used to store representative data about the patient's use of the PEMF system based on the internally maintained clock and calendar. The 4-character, 7-segment display module 45 is a standard integrated display module package.

The interval timer/pulse counter IC 46 is an Intel 82C54 that includes two general purpose counters controlled by the PEMF processor, executing the PEMF program, to establish the duty cycle of the pulse output.

The pulse output, in turn, controls the energization and de-energization of the transducers, and thereby determines the activation of the magnetic fields used in the PEMF therapy.

For the exemplary embodiment, the PEMF program causes the interval timer/pulse counter IC 46 to output a variable programmed train of, for example, 99 pulses lasting 25,740 microseconds, with a pulse period of 65 microseconds on and 195 microseconds off. That is, for each pulse, the transducers are energized for 65 microseconds and then de-energized (recovery phase) for 195 microseconds. A pulse train is output to the transducers every 667,000 microseconds (every 667 milliseconds or one third of a second).

The pulse trains from the interval timer/pulse counter 46 are input to the transducer drive amplifier 51, which controls the drive electronics.

Drive electronics 60 controls activation of the contoured triangular transducer 70, and the generation of the PEMF fields. The transducer is represented by a primary winding 71, a secondary winding 72 and a sense winding 73.

Drive electronics 60 includes an FET switch 64 having its control gate coupled to the control electronics, specifically transducer drive amplifier 51. The FET switch controls the activation current through the primary windings 71, thereby controlling the energization and de-energization of the contoured triangular transducer.

When FET switch 62 is switched on (during a 65 microsecond on pulse), activation current from the battery 55 flows through the primary windings, energizing the transducer. When switched off (during the 195 microsecond off period), current flows through the secondary windings as the transducer is de-energized.

The other end of primary winding 71 is coupled back to the battery 55, as is the corresponding end of the secondary winding 72 through energy recovery diode 81 (the other end of the secondary winding is grounded). A parallel-coupled group of four energy recovery capacitors 84 release energy during transducer energization, and store energy during transducer de-energization. Thus, the energy recovery capacitors 84 and the diode 81 form an energy recovery circuit that operates in conjunction with the secondary winding to provide energy recovery, thereby conserving battery power.

The sense winding for the triangular transducer is coupled back to the control electronics 40, and specifically through the field sense amplifier 52 to the PEMF processor 41. The field sense amplifier senses the electromagnetic fields generated during transducer activation, and provides feedback to the PEMF processor for monitoring the PEMF operation. The PEMF processor causes appropriate monitoring data to be stored in the data memory 44, and will cause an alarm signal in the case of malfunction.

4. Shoulder Embodiment

The contoured triangular transducer system can be anatomically contoured for other areas of the skeletal system.

Figure 4:
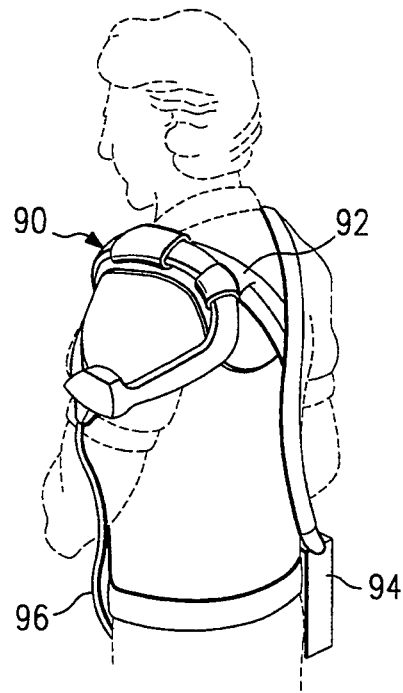
FIG. 4 shows an alternative embodiment of the PEMF contoured triangular transducer system configured for a PEMF shoulder therapy program.

FIG. 4 shows a contoured triangular transducer 90 that is anatomically contoured for providing PEMF therapy to the shoulder area. The shoulder transducer is held in place by a padded shoulder harness and body strap 92, with the integral drive electronics being coupled to a control electronics module 94 by a cable 96.

The transducer 90 has an anatomical contour that is configured for positioning over the patient's shoulder. That is, one side is curved to fit over the top of the shoulder so that corresponding angular areas are positioned in front and in back of the shoulder, with the other sides being curved down along the upper arm.

The fabrication of the shoulder transducer 90 is identical to the fabrication of the exemplary cervical transducer (FIGS. 1a-1b), except for the precise winding configuration (number of turns and wire size) and the final anatomical contouring.

5. Conclusion

Although the invention has been described with respect to a specific, exemplary embodiment, various changes and modifications may be suggested to one skilled in the art. For example, for some PEMF application, such as the exemplary cervical application (and in contrast to the shoulder embodiment), the cross sectional shape of the transducer is of less importance because the transducer shell does not directly contact the body—for those applications, a flat-wound configuration need not be employed. Also, the exemplary PEMF system is completely portable, while the advantages of the invention can be obtained from a system designed to be nonportable.

Therefore, it is intended that the invention encompass all changes and modifications that fall within the scope of the appended claims.

What is claimed is:

1. A method of fabricating a PEMF double transducer system for providing PEMF therapeutic stimulation to a target area of a patient's body, comprising the steps of:
   winding at least a primary winding with a selected number of turns around a mandrel;
   bonding said windings together into a winding bundle and removing the winding bundle from the mandrel;
   encapsulating said winding bundle in a shell that when flat, is substantially triangular in shape and malleable to allow forming the triangular-shaped, winding bundle;
   forming an anatomically contoured transducer by conformally bending said shell-encapsulated winding bundle into an anatomically contoured shape for situating on either side of the target area; and
   coupling activation electronics to said transducer for selectively activating electromagnetic fields, thereby implementing a prescribed PEMF therapy.

2. The method of fabricating a PEMF contoured triangular transducer system of claim 1, wherein:
   the step of winding at least a primary winding further includes winding a secondary winding with a selected number of turns; and
   said activation electronics including an energy recovery circuit coupled to said secondary winding for recovering energy during each activation of said transducers.

3. The method of fabricating a PEMF contoured triangular transducer system of claim 1, wherein the step of winding primary and secondary windings further includes winding a sense winding with a selected number of turns.

4. The method of fabricating a PEMF contoured triangular transducer system of claim 1, wherein the step of winding primary and secondary windings is accomplished by winding around a substantially flat mandrel, and wherein the encapsulating shell for the winding bundle has a substantially flat cross sectional profile.

5. The method of fabricating a PEMF contoured triangular transducer system of claim 4, wherein said windings are adhesive-coated magnet wire, and wherein the step of bonding said windings is accomplished by heat curing the adhesive.

6. The method of fabricating a PEMF contoured triangular transducer system of claim 1, wherein the step of encapsulating said windings comprises the steps of:

placing said bonded winding bundle in a mold with a selected shape;

injecting a shell material into said mold to encapsulate said windings in a shell that is malleable to allow forming the triangular-shaped, shell-encapsulated winding bundle into an anatomically contoured shape, and then removing the shell from the mold; and bending said shell into a selected anatomical contour.

7. The method of fabricating a PEMF contoured triangular transducer system of claim 6, wherein the step of injecting a shell material further comprises the steps of:

preparing a shell material in a partial vacuum to substantially eliminate entrapped air from the material;

injecting said shell material into the mold in a partial vacuum to substantially eliminate entrapped air, encapsulating said windings in a shell that is malleable but substantially rigid once forces used to form the triangular-shaped, shell-encapsulated winding bundle into an anatomically contoured shape have been removed; and removing said transducer from the mold.

8. The method of fabricating a PEMF contoured triangular transducer system of claim 1, further including, before the step of encapsulating, the step of attaching to said winding bundle at least a portion of said activation electronics for encapsulation with said winding bundle.

9. A method of fabricating a transducer system for providing electromagnetic therapeutic stimulation to a target area of a patient's body, comprising the steps of:

winding at least a primary winding with a selected number of turns around a mandrel;

bonding said windings together and removing the winding bundle from the mandrel;

encapsulating said winding bundle in a shell that is malleable and is substantially triangular in shape; and coupling control electronics to said shell-encapsulated winding bundle for selectively generating electromagnetic fields, thereby implementing a prescribed electromagnetic therapy.

10. The method of fabricating a triangular transducer system of claim 9, wherein the step of winding at least a primary winding further includes winding a secondary winding with a selected number of turns.

11. The method of fabricating a triangular transducer system of claim 10, wherein the step of winding at least a primary winding and a secondary winding further includes winding a sense winding with a selected number of turns.

12. The method of fabricating a triangular transducer system of claim 10, wherein the step of winding at least a primary winding and a secondary winding is accomplished by winding around a substantially flat mandrel, and wherein the encapsulating shell for the winding bundle has a substantially flat cross sectional profile.

13. The method of fabricating a triangular transducer system of claim 12, wherein said windings are adhesive-coated magnet wire, and wherein the step of bonding said windings is accomplished by heat curing the adhesive.

14. The method of fabricating a triangular transducer system of claim 9, wherein the step of encapsulating said windings comprises the steps of:

placing said bonded winding bundle in a mold with a substantially triangular shape; and injecting a shell material into said mold to encapsulate said windings in a shell that is malleable, and then removing the shell from the mold.

15. The method of fabricating a triangular transducer system of claim 14, wherein the step of injecting a shell material comprises the steps of:

preparing a shell material in a partial vacuum to substantially eliminate entrapped air from the material;

injecting said shell material into the mold in a partial vacuum to substantially eliminate entrapped air, encapsulating said windings in a shell that is malleable; and removing said shell from the mold.

16. The method of fabricating a triangular transducer system of claim 9, further including, before the step of encapsulating, the step of attaching to said winding bundle at least a portion of said control electronics for encapsulation with said winding bundle.

* * * * *